United States Patent [19]

King

[11] Patent Number: 5,064,624
[45] Date of Patent: Nov. 12, 1991

[54] TWO PHASE DISPENSER

[76] Inventor: Joseph A. King, 16261 South Temple Dr., Minnetonka, Minn. 55343

[21] Appl. No.: 414,473

[22] Filed: Sep. 29, 1989

[51] Int. Cl.[5] .............................................. B01D 1/00
[52] U.S. Cl. .................................... 422/264; 137/268; 239/34; 239/57; 239/60; 422/123; 422/265; 422/276; 422/277
[58] Field of Search ............... 422/123, 265, 246, 277, 422/264; 137/268; 239/34, 57, 60

[56] References Cited

U.S. PATENT DOCUMENTS

| | | |
|---|---|---|
| 2,988,284 | 6/1961 | Smith . |
| 3,598,536 | 8/1971 | Christensen . |
| 3,617,566 | 11/1971 | Oshima et al. . |
| 3,861,991 | 1/1975 | Kim . |
| 3,904,528 | 9/1975 | Yocum . |
| 4,172,039 | 10/1979 | Akiyama . |
| 4,217,331 | 8/1980 | Schaub . |
| 4,241,025 | 12/1980 | Grayson IV. et al. ............. 422/265 |
| 4,286,754 | 9/1981 | Jones . |
| 4,419,326 | 12/1983 | Santini . |
| 4,454,987 | 6/1984 | Mitchell . |
| 4,630,634 | 12/1986 | Sasaki et al. . |
| 4,702,270 | 10/1987 | King Sr. . |

Primary Examiner—Robert J. Warden
Assistant Examiner—Timothy M. McMahon
Attorney, Agent, or Firm—Jacobson & Johnson

[57] ABSTRACT

A two phase floating dispenser for simultaneously dispensing chemicals into two different fluid mediums with the dispenser having a submerged portion and an unsubmerged portion to permit the transfer of materials between the fluid medium that supports the floating dispenser and the submerged portion of the floating dispenser and between the atmosphere surrounding the unsubmerged portion of the floating dispenser and the unsubmerged portion of the floating dispenser so that a user can simultaneously transfer at least two materials between two different fluid mediums.

15 Claims, 1 Drawing Sheet

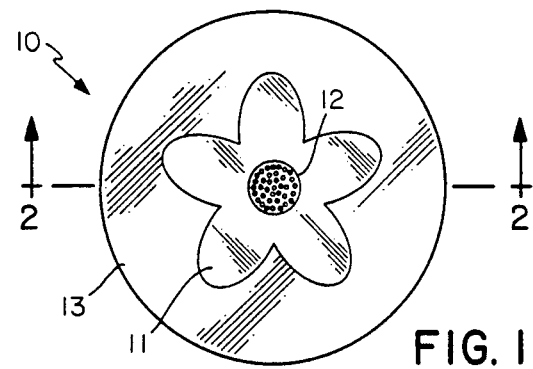
FIG. 1
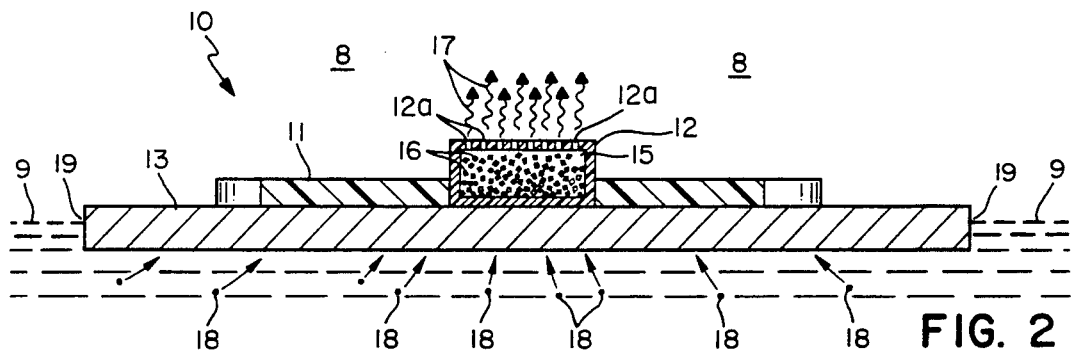
FIG. 2
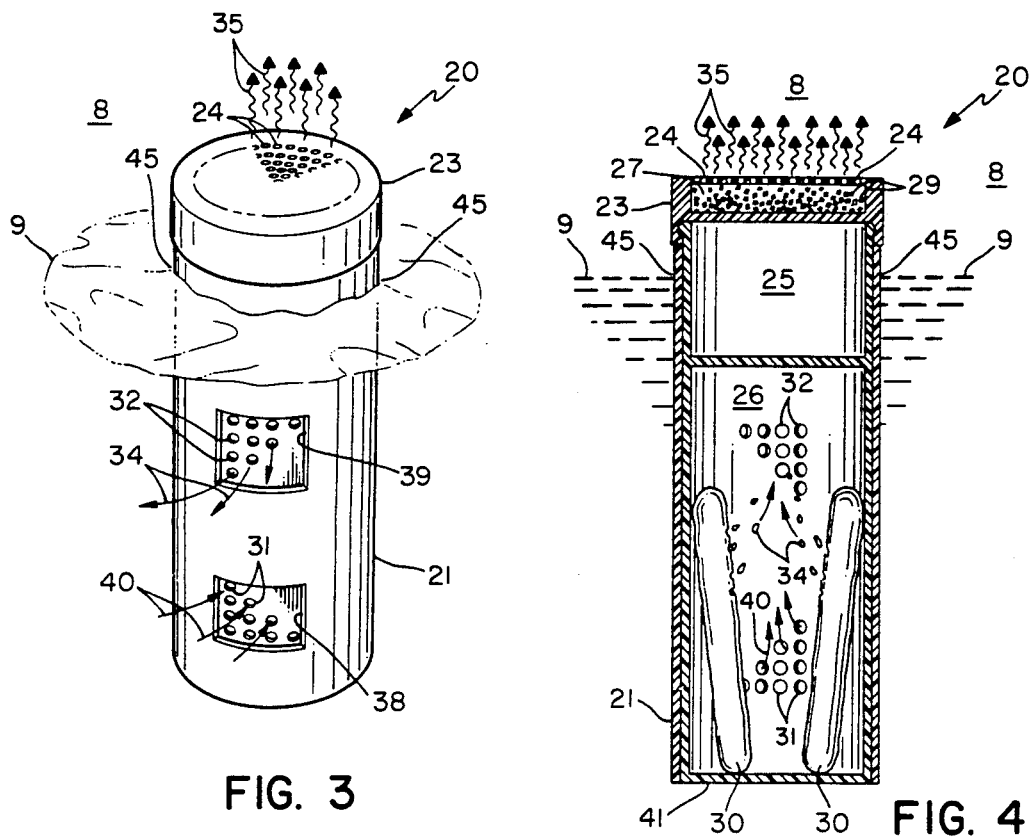
FIG. 3
FIG. 4

TWO PHASE DISPENSER

FIELD OF THE INVENTION

This invention relates generally to dispensers and, more particularly, to floating dispensers for transfer of chemicals between the dispenser and the fluid mediums surrounding the floating dispenser.

BACKGROUND OF THE INVENTION

The concept of floating dispensers for dispensing chemicals such as bromine into a pool or the like is known in the art. Also, it is known to dispense materials such as fragrances into the atmosphere through conversion of the fragrance into a vapor that is dispersed in the air. The present invention provides an improvement to the dispenser art by providing in one embodiment a two phase floating dispenser that simultaneously disperse chemicals into the air and into the pool water. The two phase dispensers floats partially submerged in a fluid medium such as a swimming pool, spa, or the like. The two phase dispenser has a submerged portion (located below the water line) and a nonsubmerged portion (located above the water line) so that the dispenser can simultaneously dispense a water dispersible chemical directly into the water that supports the floating dispenser and directly dispense an air dispersible chemical into the air surrounding the nonsubmerged portion of the floating dispenser. In normal operation the air receives a fragrance or the like and the water is disinfected. In another embodiment of my floating two phase dispenser I simultaneously draw the body oils from the pool into the dispenser while emitting a fragrance into the surrounding atmosphere.

DESCRIPTION OF THE PRIOR ART

The Christensen U.S. Pat. No. 3,598,536 shows a floating chemical feeder that dispenses a dispersible chemical into the water through a slot located in a floating feeder.

The Schaub U.S. Pat. No. 4,217,331 shows a float dispenser that contains a chemical tablet that dissolves and releases chlorine into the swimming pool.

The Sassaki U.S. Pat. No. 4,630,634 shows a floating dispenser for spas that contains a solid that dissolves in the water to release chlorine into the water as the dispenser floats in the spa.

The King U.S. Pat. No. 4,702,270 shows a floating dispenser that dispenses a chemical directly into the water.

The Kim U.S. Pat. No. 3,861,991 shows an artificial flower that contains a reservoir of perfume that is emitted to the surrounding atmosphere through a wick. The reservoir of perfume is located in the central area of the flower.

The Jones U.S. Pat. No. 4,286,754 shows a table mounted wicking structure that dispensers volatile air freshening chemicals into the surrounding atmosphere.

The Santini U.S. Pat. No. 4,419,326 shows a table mounted vapor dispensing device that uses nylon wicks to wick a liquid to a hemispherical open cell surface where it dissipates into the surrounding atmosphere.

The Mitchell U.S. Pat. No. 4,454,987 shows a fragrance dispenser that emits a fragrance from a container to the surrounding atmosphere over an extended period of time.

The Smith U.S. Pat. No. 2,988,284 shows a porous block that contains a volatile perfume material impregnated in the block so that the block can emit the perfume over an extended period of time.

The Yocum U.S. Pat. No. 3,904,528 shows a pick up element for oily contaminates that floats on the water and absorbs oily contaminates from the water into the pick up element.

The Oshima U.S. Pat. No. 3,617,566 shows a floating bag that absorbs the oil floating on the surface of the water.

The Akiyama U.S. Pat. No. 4,172,039 shows a floating container that has an oil absorber that collects the oil from the water.

BRIEF SUMMARY OF THE INVENTION

Briefly, the present invention comprises a two phase floating dispenser with a submerged portion that provides for the transfer of materials between the fluid medium that supports the floating dispenser and the submerged portion of the floating dispenser and between the atmosphere surrounding the unsubmerged portion of the floating dispenser and the unsubmerged portion of the floating dispenser so that a user can simultaneously transfer at least two materials between two different fluid mediums.

BRIEF DESCRIPTION OF THE DRAWINGS

FIG. 1 is a top vie of the floating device.
FIG. 2 is a view of FIG. 1 alone line 2—2.
FIG. 3 is a second embodiment of the floating device.
FIG. 4 is a cut away view of FIG. 3.

DESCRIPTION OF THE PREFERRED EMBODIMENT

Referring to FIG. 1 and FIG. 2 reference numeral 10 generally identifies one embodiment of a two phase floating dispenser that simultaneously absorbs chemicals such as oils directly from the liquid medium such as water and emits a fragrance directly into a gaseous medium such as an air atmosphere. Two phase dispenser 10 comprise a circular buoyant pad 13 that floats on water 9. Numeral 19 indicates the water line and defines between the submerged portion and the unsubmerged portion of my two phase floating dispenser 10.

Located on top of pad 13 is a decorative flower that has a series of radially extending petals 11 and a central region that contains a cylindrical container 12 that holds a solid fragrance material 16. Located in the top of container 12 is a chemical transfer means that comprises a series of holes 12a that permit fragrance vapors 17 to be dispensed into the surrounding air atmosphere. That is, chemical fragrance particles 16, which are well known in the art, slowly dissolve and permit the fragrance chemicals to disperse into the surrounding air atmosphere.

The floating pad 13 comprises porous polypropylene material manufactured by Matarah Industries Inc. of Milwaukee, Wis. The material floats in water, is insoluble in water and is both oleophilic and hydrophobic. The material is similar to the material disclosed in prior art U.S. Pat. Nos. 3,617,566; 3,904,528 and 4,172,039 since they also disclose floating materials that absorb oil floating on water.

FIG. 1 illustrates that oil particles 18 are absorbed from the water directly into the submerged portion of the polypropylene pad 13 while at the same time the fragrance material 16 is being dispensed from the unsubmerged portion of the two phase dispenser into the surrounding atmosphere.

Referring to FIGS. 3 and 4 an alternate embodiment of my invention is shown that transfers a first chemical dispersant directly into the fluid medium surrounding the submerged portion of the dispenser and a second chemical dispersant directly into the air atmosphere surrounding the unsubmerged portion of my two phase dispenser.

Dispenser 20 for emitting a disinfectant chemical into the surrounding fluid medium is similar to the dispenser shown in U.S. Pat. No. 4,702,270. Dispenser 20 permits the user to simultaneously disperse a disinfectant chemical directly into the fluid medium surrounding the submerged portion of the floating dispenser and a fragrance into the air surrounding the unsubmerged portion of dispenser 20.

Dispenser 20 includes an inner cylindrical container 41 that includes a lower chemical compartment 26 with a chemical transfer means, a floatation chamber 25 and an air fragrance dispenser compartment 27 with a chemical transfer means. Located on the outside of cylindrical container 41 is a rotatable cylindrical sleeve 21 that permits the user to control the amount of material dispensed into the fluid medium surrounding the submerged portion of my two phase dispenser. The submerged portion of my two phase dispenser 20 is located below water line 45 and the unsubmerged portion is located above water line 45.

Compartment 26 includes a set of upper openings 32 and a set of lower openings 31. Located within compartment 26 are bromine sticks 30 that dissolve and transmit chemical 34 into the fluid medium which in this case is water 9 surrounding the submerged portion of compartment 26. The arrows 40 illustrate water 40 as it circulates through opening 38 and holes 31 into compartment 26 where it picks up dissolved bromine 30. The arrows 34 in FIG. 3 illustrate the chemical 30 being dispersed into the water 9 surrounding the floating dispenser. While bromine is illustrated as the chemical dispersed into the water other chemicals could also be dispersed into the water from the submerged portion of my dispenser.

Chamber 25 comprises an air filled sealed compartment that provides sufficient buoyancy so that my two phase floating dispenser floats partially submerged in a spa, pool or the like. If desired compartment 25 could be filled with a buoyant material.

Located on top of my two phase dispenser 20 is is a container 23 that has a compartment 27. Container 23 has a plurality of cylindrical openings 24 that permit vapors from a fragrance 29 located in compartment 27 to be directly dispensed into the surrounding atmosphere. FIG. 4 shows solid fragrance particles 29 located in compartment 27. The solid fragrance 29 dissolve in the air and dissipates into the surrounding atmosphere as vapor 35.

Thus the two phase dispenser 20 simultaneously permits the user to dispense a fragrance or the like directly from the unsubmerged portion of the dispenser into the surrounding air atmosphere while the submerged portion of the dispenser dispenses a disinfectant chemical directly into the water through the portion of the dispenser that is submerged in the water that supports the two phase dispenser. If the chemicals used in the unsubmerged portion and the submerged portion take approximately the same time to dissipate then the dispenser can be discarded with out wasting appreciable chemicals.

Typically, I prefer to have chemicals that may take up to six weeks to completely dissipate under normal conditions.

While my dispenser is shown dispensing a fragrance and a disinfectant other chemicals could be dispensed with my two phase dispenser. For example, colorants could be dispensed into the water and air freshening and disinfectant chemicals could be dispensed into the air.

I claim:

1. A two phase floating dispenser that floats in a liquid medium which is located in a gaseous medium comprising:

a floating member, said floating member having flotation means for providing sufficient buoyancy so that said floating member floats partially submerged in the liquid medium, said floating member having a submerged portion submerged in the liquid medium and an unsubmerged portion exposed to the gaseous medium, said floating member including means for holding at least two different chemicals;

a first chemical located in said means for holding at least two different chemicals with said first chemical being dispersible in the gaseous medium, said means for holding at least two different chemicals operable to permit simultaneous transfer of a second chemical between the liquid medium and the submerged portion of the floating dispenser and said first chemical between the unsubmerged portion of the floating member and the gaseous medium, said means for holding at least two different chemicals in said floating member including first chemical transfer means located in said exposed portion to permit said first chemical dispersible in a gaseous medium to be dispersed from said unsubmerged portion into the gaseous medium, said floating member including second chemical transfer means located in said submerged portion to transfer a second chemical between said submerged portion of said floating member and the liquid medium as said floating member floats in the liquid medium.

2. The two phase dispenser of claim 1 wherein said flotation means for providing sufficient buoyancy includes an oleophilic and hydrophobic material.

3. The two phase dispenser of claim 2 including a second chemical in said floating dispenser so that said second chemical can be dispersed into said liquid medium.

4. The two phase dispenser of claim 2 wherein said oleophilic and hydrophobic material comprises a porous polypropylene.

5. The two phase dispenser of claim 1 wherein said chemical dispersible in a gaseous medium comprises a fragrance emitting chemical.

6. The two phase dispenser of claim 5 wherein said unsubmerged portion is in the shape of a flower with said flower having a central region with said chemical dispersible in a gaseous atmosphere located in said central region.

7. The two phase dispenser of claim 6 wherein said oleophilic and hydrophobic material has a circular shape with said flower centrally located on said material.

8. The two phase dispenser of claim 1 wherein said floating dispenser includes a compartment for holding a liquid disperseable chemical disinfectant to be dispersed into said liquid medium.

9. The two phase dispenser of claim 8 wherein said two phase dispenser includes control means to adjust the amount of at least one of the chemicals being dispersed from said two phase dispenser.

10. The two phase dispenser of claim 9 wherein said disinfectant material is a solid chemical that dissolves into said liquid medium.

11. The two phase dispenser of claim 10 including a solid fragrance chemical to be dispersed into said gaseous medium as a vapor.

12. A two phase floating chemical dispenser for simultaneously dispensing chemicals into water and air comprising:
- a floating member, said floating member including a floatation compartment to permit said floating member to float partially submerged in water to create a water submerged portion and an air exposed portion, said floating member including an air exposed compartment to hold a chemical dispersible in air and a water exposed compartment to hold a chemical dispersible in water, said air exposed compartment including means to permit a chemical dispersible in air to be transferred from said air exposed compartment to the air and said water submerged compartment including a water dispersible chemical and further means to permit transfer of said water dispersal chemical into the water;
- a first air dispersible chemical, said first air dispersible chemical located in said air exposed compartment; and
- a second water dispersible chemical, located in said water submerged portion so that said said floating dispenser can dispense chemicals into both the air and the water.

13. The two phase floating dispenser of claim 12 wherein said air dispersible chemical comprises a fragrance and said water dispersible chemical comprise a disinfectant.

14. The two phase floating dispenser of claim 13 wherein said air dispersible chemical and said water dispersible chemical have substantially the same dissolving rates so that both said air dispersible chemical and said water dispersible chemical are substantially dispersed after a predetermined length of time so that the user can discard said floating dispenser without having wasted said water dispersible chemical and said air dispersible chemical.

15. A two phase floating dispenser for dispensing an air dispersible chemical into the air and for removing an oil from oil floating on water comprising:
- a floating member, said floating member including a first oleophilic member partially submerged in water, said first oleophilic member for removing oil floating on the water said flotation member including a second compartment for holding a fragrance emitting chemical;
- a fragrance emitting chemical locate in said second compartment, said second compartment located in the air so that the fragrance emitting chemical located in said second compartment can be dispensed from said second compartment into the air to permit the user to have a dispenser for providing for removing oil from the water and for providing a fragrance to the air.

* * * * *